United States Patent
Lavi

(10) Patent No.: US 7,447,535 B2
(45) Date of Patent: Nov. 4, 2008

(54) MAPPING THE CORONARY ARTERIES ON A SPHERE

(75) Inventor: Guy A. Lavi, Nordia (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 15 days.

(21) Appl. No.: 10/567,237

(22) PCT Filed: Jul. 26, 2004

(86) PCT No.: PCT/IB2004/002569

§ 371 (c)(1),
(2), (4) Date: Feb. 3, 2006

(87) PCT Pub. No.: WO2005/011500

PCT Pub. Date: Feb. 10, 2005

(65) Prior Publication Data

US 2006/0235288 A1      Oct. 19, 2006

Related U.S. Application Data

(60) Provisional application No. 60/514,928, filed on Oct. 28, 2003, provisional application No. 60/492,391, filed on Aug. 4, 2003.

(51) Int. Cl.
*A61B 5/05*     (2006.01)
*G06K 9/00*     (2006.01)

(52) U.S. Cl. .................... 600/407; 382/128
(58) Field of Classification Search ........... 600/407; 382/128, 169, 190, 237; 345/418
See application file for complete search history.

(56) References Cited

U.S. PATENT DOCUMENTS 4,882,679 A    11/1989    Tuy et al.

(Continued)

FOREIGN PATENT DOCUMENTS

EP     0 983 747 A1    3/2000

(Continued)

OTHER PUBLICATIONS

Kirbas, C., et al.; Vessel Extraction Techniques and Algorithms: A Survey; 2003; Proc. Of IEEE Symp. On BioInformatics and BioEngineering; pp. 238-245.

(Continued)

*Primary Examiner*—Eric F Winakur
*Assistant Examiner*—Michael T Rozanski

(57) ABSTRACT

A coronary arteries tree is approximated by a base sphere (32) which is best fitted to vessels centerlines (38). The base surface (32) is gridded to define pixels (52). The base sphere (32) is mapped to fit the centerlines (38) such that a true form surface (56) is determined. A wall thickness to the true form surface (56) is defined, preferably, by a user. A normal of each pixel (52) is searched for grayscale values of voxels. Each pixel (52) is assigned a maximum of grayscale values of voxels within the defined wall thickness intersected by the corresponding normal. The resulting true form surface is undistorted mode of visualization revealing the arteries tree in its context running on the true surface drawn through the vessels. Mapping the assigned grayscale values onto the base sphere (32) visualizes arteries tree on a globe surface (84) which might be rotatably inspected as a globe. Mapping the assigned grayscale values into a flat surface visualizes arteries tree on a two-dimensional map.

19 Claims, 6 Drawing Sheets

U.S. PATENT DOCUMENTS

| | | | | |
|---|---|---|---|---|
| 5,175,773 | A | 12/1992 | Garreau et al. | 382/6 |
| 5,594,766 | A | 1/1997 | Tam | 378/4 |
| 5,793,375 | A * | 8/1998 | Tanaka | 345/426 |
| 6,047,080 | A | 4/2000 | Chen et al. | 382/128 |
| 6,377,835 | B1 | 4/2002 | Schoenberg et al. | 600/419 |

FOREIGN PATENT DOCUMENTS

| | | |
|---|---|---|
| EP | 1 031 943 A2 | 8/2000 |
| JP | 2001-178725 A | 7/2001 |
| WO | WO03/046835 A1 | 6/2003 |

OTHER PUBLICATIONS

Sun, Y., et al.; Performace Analysis of Maximum Intensity Projection Algorithm for Display of MRA Images; 1999; IEEE Trans. On Medical Imaging. 18(12)1154-1169.

Breeuwer, et al.; Analysis of Volumetric Cardiac CT and MR Image Data; 2003; MedicaMundi; 47/2.

* cited by examiner

MAPPING THE CORONARY ARTERIES ON A SPHERE

CROSS REFERENCE TO RELATED APPLICATIONS

This application claims the benefit of U.S. provisional application Ser. No. 60/492,391 filed Aug. 4, 2003, and U.S. provisional application Ser. No. 60/514,928 filed Oct. 28, 2003, which are both incorporated herein by reference.

The present invention relates to the anatomical imaging arts. It finds application in conjunction with the display of the entire coronary tree in the heart context and will be described with particular reference thereto. Of course, the technique is also applicable to mapping other anatomical regions, such as the cerebral cortex. Although described with particular reference to CT tomography, it will further be appreciated that the invention is equally applicable to other diagnostic imaging techniques which generate two and three-dimensional digital diagnostic images including coronary arteries for analysis.

A variety of imaging modalities can be used to determine structural, functional and perfusion characteristics of the heart and coronary arteries. Substantial research and development have been concentrated on new technologies and methods that can aid the diagnosis and analysis of the coronary arteries, and on planning appropriate treatment. Much of this effort has been focused on the improvement of the visualization of the coronary arteries and the development of computer-assisted analysis of the resulting images.

Imaging and analysis of the coronary arteries serve several purposes: visualization of the coronary tree, detection and quantification of stenosis, quantification of the coronary tree reserve, and analysis of the vessel walls. Traditionally, x-ray angiography has been used to detect and quantify stenosis in the coronary arteries. The development of multi-slice CT scanner technology having increasingly improved resolution particularly in the slice direction made the CT imaging of vascular systems attractive for clinical applications. Multi-slice detectors allow several slices to be acquired and processed simultaneously enabling more accurate quantification of stenosis.

Many visualization techniques and quantification strategies are currently in use. One approach is the construction of multi-planar reformatted images (MPR) and/or slab maximum intensity projections (slab-MIP) in optimally chosen planes, so that the major segments of the coronary tree are visualized. In addition, the CT's ability of acquiring 3D volumetric images can be used to acquire volume rendered images for visualizing an isolated coronary arteries tree. However, the current methods for coronary arteries inspection, e.g. curved MPR visualization of a single vessel, the planar slab MIP visualization and the volume-rendered visualization of an isolated tree either lack the completeness or the context of the coronary tree.

There is a need for a visualization technique that will allow the volumetric display of the entire coronary arteries tree in context, i.e., location, connectivity and surroundings. The present invention provides a new imaging apparatus and method which overcomes the above-referenced problems and others.

In accordance with one aspect of the present invention a diagnostic imaging system for displaying a vessel tree is disclosed. A means defines a base surface. A means grids the base surface to define pixels. A means projects along a normal of each pixel. A means assigns each pixel a grayscale value based on grayscale value of voxels intersected by a corresponding normal.

In accordance with another aspect of the present invention a method of displaying the coronary arteries tree is disclosed. A base surface is defined. The base surface is gridded to define pixels. A normal of each pixel is projected along. Each pixel is assigned a grayscale value based on grayscale value of voxels an associated normal intersected. A true surface is determined.

One advantage of the present invention resides in displaying the entire coronary arteries tree in its context.

Another advantage resides in using a closed non-planar surface as a base for displaying the data of interest.

Another advantage resides in minimization of distortions in the visualization modes.

Another advantage resides in enabling the user to explore the entire structure of the cardiovascular system at once.

Another advantage resides in permitting the user to adjust the thickness of the slab MIP to include more or less data in the image presented.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not be construed as limiting the invention.

Figure 1:
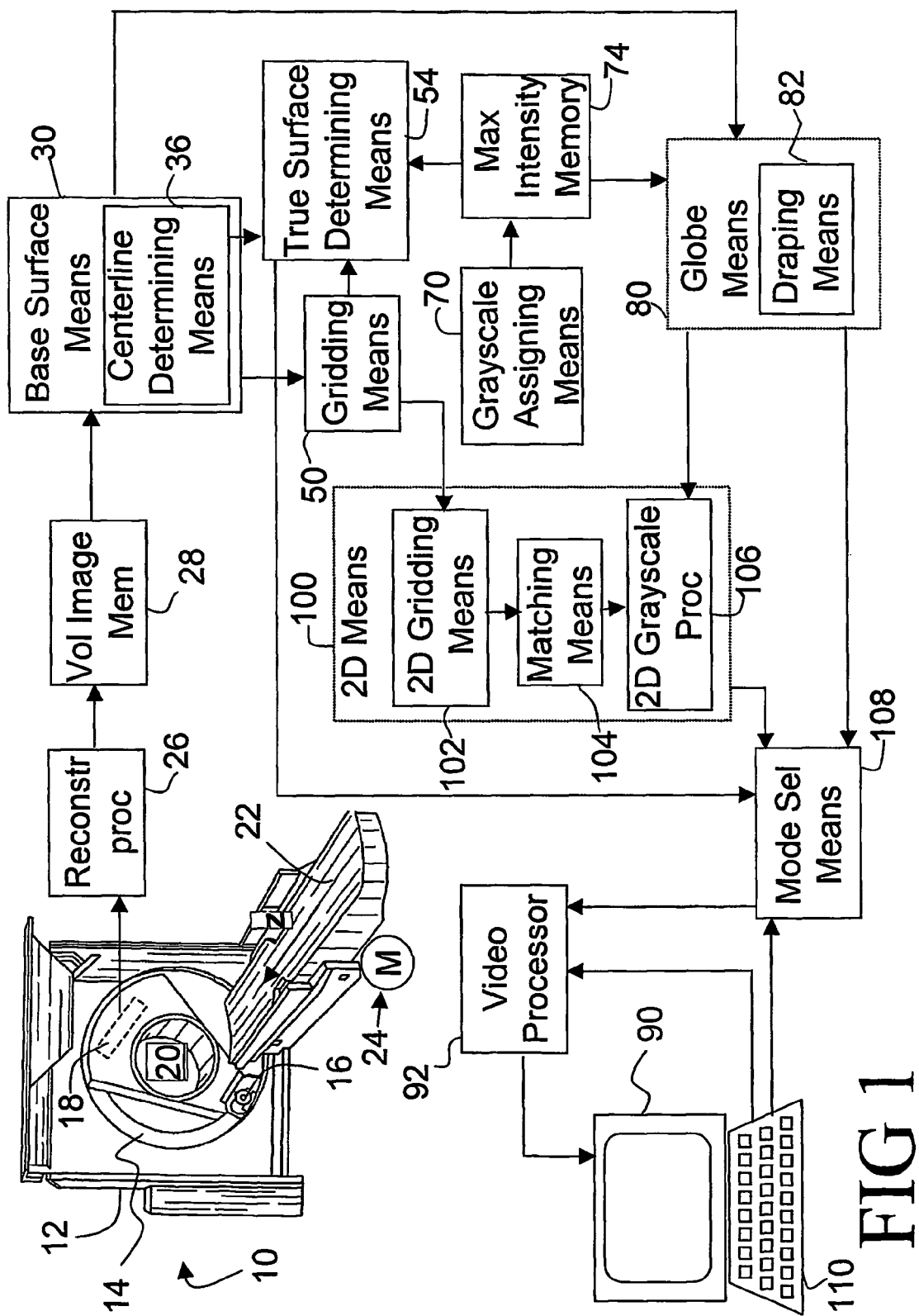
FIG. 1 is a diagrammatic illustration of a diagnostic imaging system in accordance with the present invention.

With reference to FIG. 1, a diagnostic imaging apparatus 10 generates electronic diagnostic image representations. In the preferred embodiment, the diagnostic imaging apparatus 10 includes a CT scanner which generates a three-dimensional volumetric image representation which is made up of voxels whose position is defined along orthogonal axes. Other diagnostic imaging systems, such as magnetic resonance imaging, PET imaging, SPECT imaging, and other diagnostic techniques which generate analogous three-dimensional diagnostic images are also contemplated.

In the preferred embodiment, the CT scanner includes a stationary gantry 12, in which a rotating gantry 14 is mounted. The rotating gantry carries an x-ray tube 16 and a two-dimensional array of detectors 18, which are diametrically opposed to each other across a scan circle or an examination region 20. A subject support 22 supports a region of interest of the subject in the examination region 20. Prior to imaging, the subject is preferably injected with a known contrast agent that produces the voxels of the known intensity in the vessels, preferably, at the intensity higher than that of tissue. A longitudinal drive motor 24 moves the subject support 22 longitudinally through the examination region 20. Preferably, the subject support 22 longitudinally reciprocates the subject as the rotating gantry 14 rotates continuously for spiral scanning. The imaging apparatus generates a volumetric image representation of a transverse volume of the subject, which includes the subject's heart, or other region of interest. Alternately, the subject support 22 can be stepped and data can be collected along a series of parallel, transverse slices. Although the detector array 18 is illustrated as rotating with the rotating gantry 14, the detector array 18 may optionally be mounted as a continuous ring on the stationary gantry 12.

A three-dimensional reconstruction processor 26 reconstructs the output signals from the detector array 18 in accordance with the angular position of each detector element, the angular position of the x-ray tube 16, and the longitudinal position of the subject support 22 at the time of sampling into one or more three-dimensional image representations; The reconstructed image representation is stored in a volumetric image memory 28.

Figure 2:
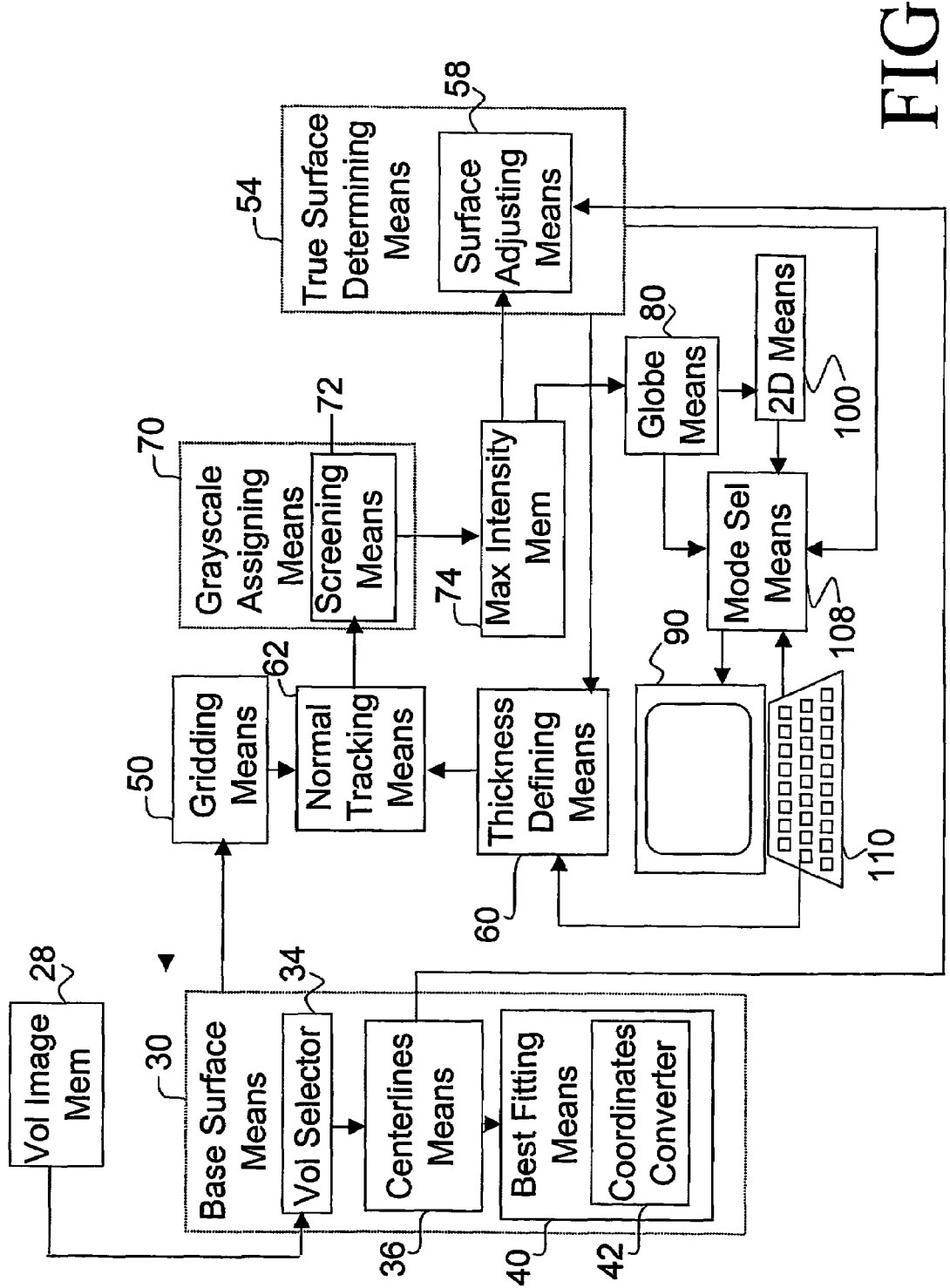
FIG. 2 is a diagrammatic illustration of a portion of a diagnostic imaging system in accordance with the present invention.
Figure 3:
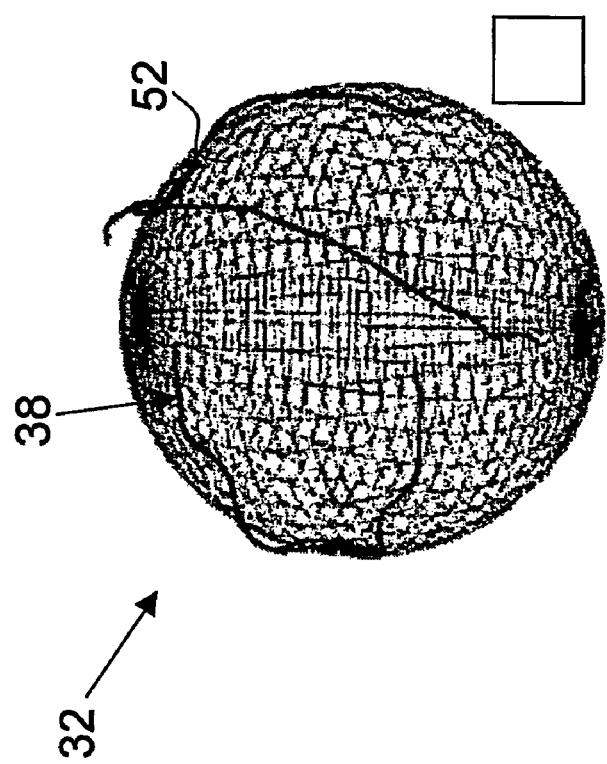
FIG. 3 is an illustration of a base sphere gridded in accordance with the present invention and arteries in the vicinity of the sphere.

With continuing reference to FIG. 1 and further reference to FIGS. 2 and 3, a base surface means or processor 30 approximates a base surface 32, which is preferably a sphere. Of course, other surfaces such as ellipsoids, anatomical heart approximations, and the like, are also contemplated. The approximation is based on the assumption that the coronary arteries lie on a substantially smooth closed surface. More specifically, a volume selecting means 34 selects a volume of data from the volume memory 28 which corresponds to the region of interest, e.g. heart, brain, or other organ. A centerlines determining means 36 finds the centerlines 38 of the vessels in the selected volume by one of known techniques. A best fitting surface means or process 40 draws a best fitted surface, preferably the sphere or ellipsoid, to the determined centerlines. Some of vessels will lie above the surface of the base surface 32, some of the vessels will lie underneath it, and some will have a portion above and a portion below the surface. The sphere or ellipsoid is rotated such that the axis of rotation is substantially parallel to a long axis of the left ventricle. In performing the best fitting process 40, a centerlines coordinates converting means 42 converts the centerlines coordinates to spherical coordinates according to equations 1.

$$\phi = a\tan[Z/\sqrt{(X^2+Y^2)}]$$
$$\mu = a\tan[Y/X]$$
$$h = [\sqrt{(X^2+Y^2)}/\cos\phi] - R$$

Equations 1 where $\phi$ is the latitude; $\lambda$ is the longitude; h is the distance from the sphere; X, Y, Z are the Cartesian coordinates of a centerline point; and R is the radius of the sphere.

Figure 4:
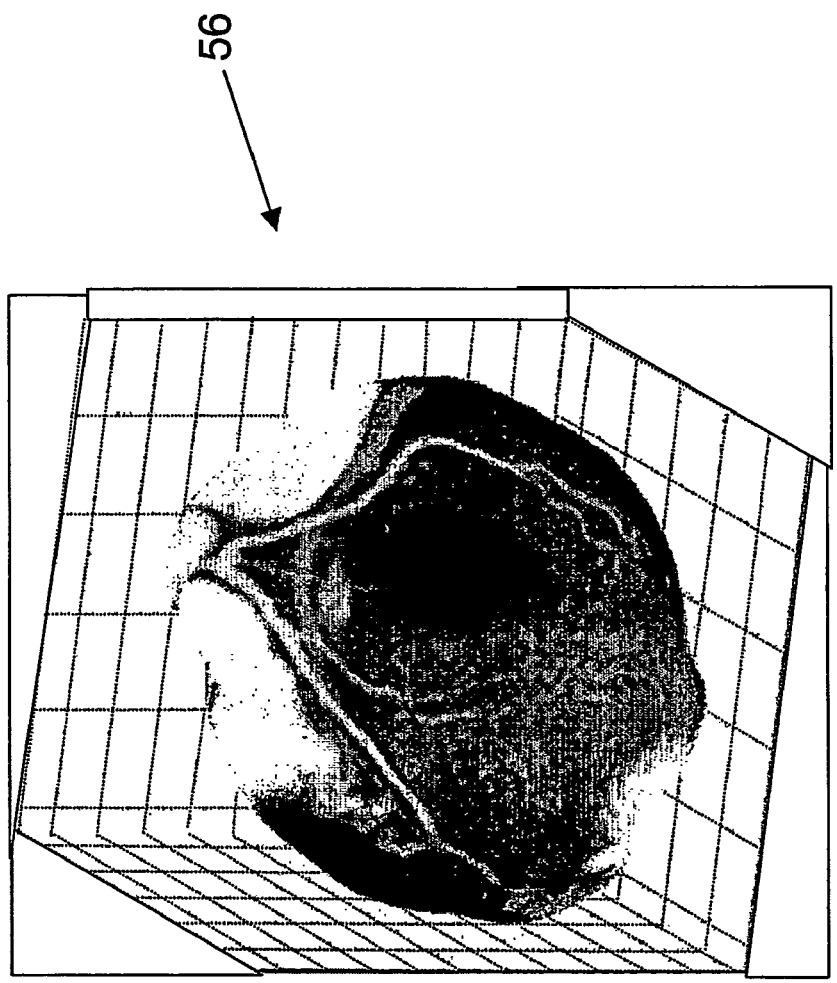
FIG. 4 is an illustration of a coronary arteries tree in a true amorphous surface form.

With continuing reference to FIGS. 1, 2 and 3, a gridding means 50 spreads a grid over the base surface 32 to grid the sphere, or other determined surface, into pixels 52. The base surface 32 is stretched or shrunk along the sphere normals to fit the true form of the vessels wherever a centerline is located such that the stretched surface lies on the centerlines. With further reference to FIG. 4, the stretching and shrinking of the sphere to fit the centerlines is performed by a true surface determining means 54 which builds a true surface 56 representing a "True Form" undistorted mode visualization, in which the coronary arteries tree in its context is revealed over a true form surface running through its vessels. More specifically, a surface adjusting means 58 receives the centerlines information from the centerline means 36 and moves the location of the spherical base surface 32 along the normals, perpendicularly to the surface, to the point where the normals intersected associated centerlines of the vessels. The remainder of the spherical base surface is mapped in and out to define the smoothly varying true form surface. The resulting true surface is the arbitrary, amorphous surface, as seen in FIG. 4.

A thickness determining means 60 determines a wall thickness of the true surface 56. Preferably, a user supplies predetermined thickness value to the thickness determining means 60, e.g. the thickness of the hollow true form volume. Alternatively, the thickness is determined by the thickness determining means 60 based on specified criteria, such as vessel diameter, or other characteristics of the subject. A normal projecting or tracking means 62 projects a normal from each pixel 52 orthogonally with respect to the true surface 56 in both directions, e.g. outward and inward from the true surface 56, to the limits of the wall thickness determined by the thickness determining means 60. A grayscale assigning means 70 examines the intensity of each voxel along the normal and assigns a grayscale or intensity value to the corresponding pixel of the true surface 56 to be displayed in the resultant image. A screening means 72 screens the grayscale values of voxels, intersected by each normal, based on predetermined criteria to select a grayscale intensity value which will be displayed for the corresponding pixel. In the preferred embodiment, the screening means 72 selects a maximum intensity value along each normal and stores it in a maximum intensity image pixel memory 74. The cycle repeats until all the normals are screened and a grayscale value of each pixel is determined.

Figure 5:
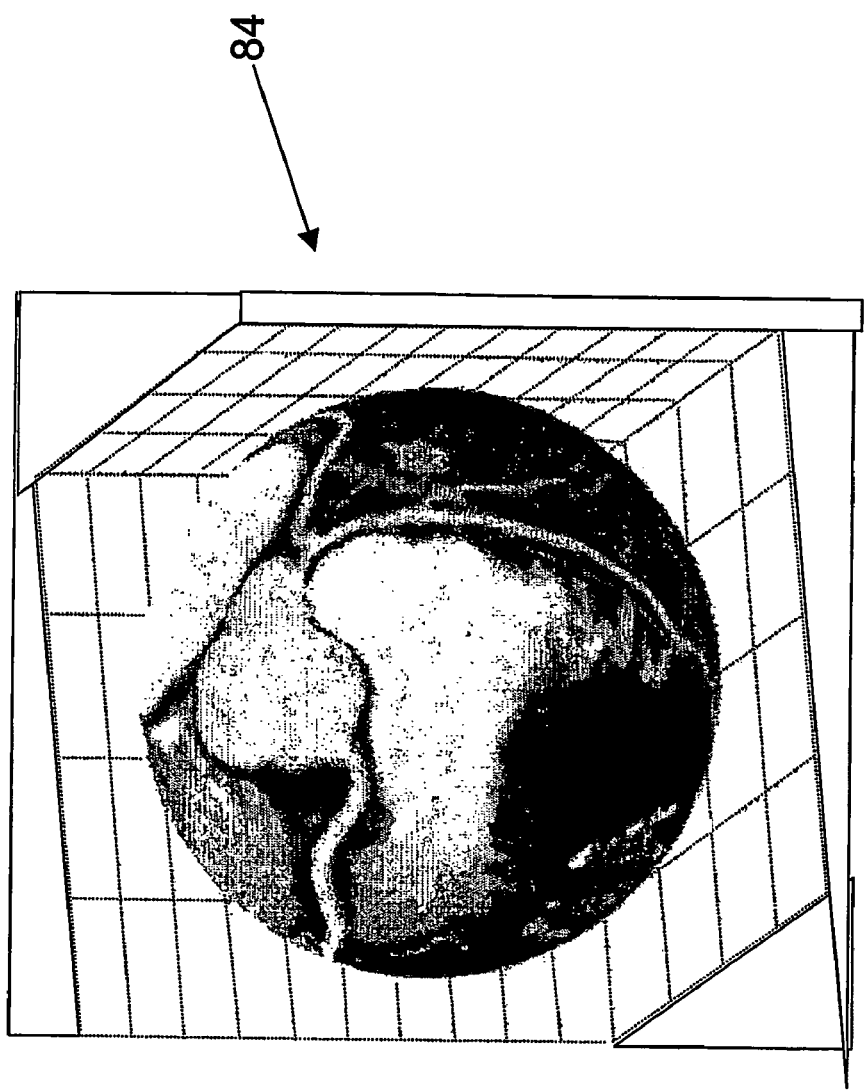
FIG. 5 is an illustration of a coronary arteries tree in a globe surface form.

With continuing reference to FIG. 1 and further reference to FIG. 5, a globe means 80 presents a "Globe" mode of visualization, in which the coronary arteries tree is shown on a sphere which is best fitted to the determined amorphous true surface 56. More specifically, a draping means 82 drapes or projects the grayscale values, which have been assigned by the grayscale assigning means 70 to the true form surface onto the spherical base surface by projecting the voxels along the normal to the sphere corresponding to each spherical or globe surface pixel. The resulting surface is a globe like structure 84 and may be rotatably examined as a globe.

To display the "True Form" or "Globe" on a conventional monitor 90 having a two-dimensional display, a video processor 92 projects a normal from each pixel of the display. Each display pixel is assigned the grayscale value of the true surface or the globe surface that it intersects. It will be noted that surface pixels closest to the viewing screen are displayed substantially undistorted, while surface pixels toward the poles and the periphery become progressively more compressed to give the viewer the impression of viewing a 3D object on the 2D viewing screen. Optionally, the 3D effect can be enhanced by assigning an illumination direction and adding shading.

Figure 6:
FIG. 6 is a 2D map of a coronary arteries tree.

With continuing reference to FIG. 1 and further reference to FIG. 6, a 2D means 100 maps the globe 84 or a selected portion of it on a flat surface analogous to the way that the round surface of the earth is projected onto flat maps. More specifically, a 2D gridding means 102 spreads the original grid of the base surface 32 on a 2D x-y surface. Typically, equatorial surface pixels are substantially undistorted, while more polar surface pixels are stretched to maintain spatial relationships. A matching means 104 matches each coordinate of the base surface 32 to corresponding coordinates on the x-y viewing plane. A 2D grayscale processor or means 106 assigns each pixel on the x-y viewing surface a grayscale value of the corresponding pixel from the globe surface 84.

A mode selection means 108 receives an input from a user and selects a visualization mode for processing. The selected visualized data is processed by the video processor 92 and displayed then on a monitor 90. A user input device 110, such as a keyboard, enables the user to control the video processor 92 to display selected projections, rotate the globe or true surface, and input necessary information as was discussed above.

In one alternate embodiment, the true form surface and its wall thickness are defined, but then data is projected directly onto the spherical (or elliptical) base surface. In another alternate embodiment, the two dimensional image is mapped directly from the true form image rather than the globe image, which was derived from the true form image.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging system for displaying a vessel tree comprising:
    a means for defining a base surface, wherein the base surface is a sphere or an ellipsoid, the means for defining a base surface including:
        a means for determining vessels centerlines from image data;
        a means for mapping the base surface to the centerlines to define a true form surface;
    a means for gridding the base surface to define pixels;
    a means for projecting along a normal of each pixel; and
    a means for assigning each pixel a grayscale value based on grayscale value of voxels in the image data intersected by a corresponding normal.

2. The system as set forth in claim 1, further including:
    a means for defining a wall thickness to the true form surface.

3. The system as set forth in claim 2, wherein the grayscale assigning means assigns each pixel a maximum of grayscale values of voxels within the defined wall thickness intersected by the corresponding normal.

4. The system as set forth in claim 1, further including:
    a means for determining a globe surface including a means for mapping the assigned grayscale values into a spherical surface.

5. The system as set forth in claim 4, further including:
    a means for projecting the globe surface into a two dimensional surface.

6. The system as set forth in claim 5, wherein the projecting means includes:
    a matching means which matches coordinates of the spherical surface to coordinates of the two dimensional surface; and
    2D grayscale processor which assigns each pixel on the two dimensional surface a grayscale value assigned to at least one corresponding pixel on the globe surface.

7. The system as set forth in claim 6, further including:
    a means for selecting at least one of the true form surface, the globe surface and the two-dimensional surface for displaying on a monitor.

8. A diagnostic imaging apparatus comprising:
    a scanner which examines a region of a subject including coronary arteries and acquires three-dimensional data;
    a reconstruction processor for reconstructing the three-dimensional image data into a volumetric three-dimensional image representation;
    the diagnostic imaging system of claim 1 for converting a portion of the three dimensional image representation into a coronary arteries tree display; and
    a display connected to the diagnostic imaging system of claim 1 for displaying the coronary arteries tree in a context of the region of interest.

9. A system, comprising:
    a base surface processor that approximates a spherically-shaped base surface;
    a volume selector that selects a volume of image data from a volume memory;
    a centerlines determiner that finds centerlines of vessels in the selected volume of image data;
    a best fitting surface process that draws a spherically shaped best fitted surface to the determined centerlines;
    a gridder that spreads a grid over the base surface, thereby gridding the sphere into pixels;
    a projector that projects a normal from each pixel; and
    an assigner that assigns each pixel a grayscale value based on grayscale value of voxels in the image data intersected by a corresponding normal.

10. The system of claim 9, wherein at least one vessel in a first set of the vessels lies above the base surface, at least one vessel in a second set of the vessels lies underneath the base surface, and a third set of vessels includes at least a first vessel that lies above the base surface and at least a second vessel that lies below the base surface.

11. The system of claim 9, further including a centerlines coordinates converter that converts centerlines coordinates to spherical coordinates.

12. The system of claim 11, wherein the centerlines coordinates converter converts the centerlines coordinates to the spherical coordinates as a function of the following: $\phi=a \tan [Z/\sqrt{(X^2+Y^2)}]$; $\lambda=a \tan [Y/X]$, and $h=[\sqrt{(X^2+Y^2)}/\cos \phi]-R$, wherein $\phi$ is a latitude; $\lambda$ is a longitude; h is a distance from the sphere; X, Y, Z are Cartesian coordinates of a centerline point; and R is a radius of the sphere.

13. The system of claim 9, wherein the volume of data corresponds to a region of interest in a superset volume of data.

14. The system of claim 13, wherein the region of interest represents an anatomical organ.

15. The system of claim 9, wherein the sphere is rotated such that an axis of rotation is substantially parallel to a long axis of a left ventricle.

16. The system of claim 9, further including a true surface determiner that at least one of stretches or shrinks the base surface along sphere normals to fit a true form of the vessels, in which the vessels are not distorted.

17. The system of claim 16, wherein the vessels represent an entire coronary arteries tree in context, including location, connectivity, and surroundings.

18. The system of claim 9, further including a screener that screens the grayscale values of voxels, intersected by each normal, based on predetermined criteria to select a grayscale intensity value which is displayed for the corresponding pixel, wherein the screener selects a maximum intensity value along each normal and stores the value in a maximum intensity image pixel memory.

19. The system of claim 9, further including a presenter that presents a coronary arteries tree on the sphere, best fitted to an amorphous true surface.

* * * * *